United States Patent [19]

Newkome et al.

[11] Patent Number: 5,136,096

[45] Date of Patent: Aug. 4, 1992

[54] MULTIFUNCTIONAL SYNTHONS AS USED IN THE PREPARATION OF CASCADE POLYMERS OR UNIMOLECULAR MICELLES

[75] Inventors: George R. Newkome; Charles N. Moorefield, both of Temple Terrace, Fla.

[73] Assignee: University of South Florida, Tampa, Fla.

[21] Appl. No.: 681,613

[22] Filed: Mar. 26, 1991

Related U.S. Application Data

[63] Continuation of Ser. No. 401,323, Aug. 31, 1989, abandoned.

[51] Int. Cl.$^5$ .................................................. C07C 215/10
[52] U.S. Cl. ..................................... 564/507; 558/408;
558/409; 558/410; 560/186; 564/201; 564/360;
568/22; 568/62; 568/308; 568/336; 568/414;
568/451; 568/497; 568/705; 568/712; 568/853
[58] Field of Search ............... 564/507, 360; 568/705,
568/712, 451, 853; 558/408, 409, 410

[56] References Cited

U.S. PATENT DOCUMENTS

| | | | |
|---|---|---|---|
| 2,139,121 | 12/1938 | Hass et al. ............................ | 260/632 |
| 2,157,391 | 5/1939 | Vanderbilt et al. ................... | 260/584 |
| 2,164,271 | 6/1939 | Hass et al. ............................ | 260/584 |
| 2,280,790 | 4/1942 | Bruson ................................ | 260/464 |
| 2,280,791 | 4/1942 | Bruson ................................ | 260/464 |
| 2,280,792 | 4/1942 | Bruson ................................ | 260/464 |
| 2,282,646 | 6/1942 | De Groote ........................... | 564/507 |
| 2,399,118 | 4/1946 | Homeyer ............................. | 260/307 |
| 2,775,622 | 12/1956 | Snow ................................... | 568/853 |
| 3,154,590 | 10/1964 | Rice et al. ............................ | 568/853 |
| 3,609,156 | 9/1971 | Munakata et al. ................... | 564/507 |
| 4,507,466 | 3/1985 | Tomalia et al. ..................... | 528/332 |
| 4,558,120 | 12/1985 | Tomalia et al. ..................... | 528/363 |
| 4,568,737 | 2/1986 | Tomalia et al. ..................... | 528/332 |
| 4,587,329 | 5/1986 | Tomalia et al. ..................... | 528/363 |
| 4,911,798 | 3/1990 | Abys et al. .......................... | 204/44 |

FOREIGN PATENT DOCUMENTS 1511911 12/1967 France .................................. 564/507

OTHER PUBLICATIONS

Rice et al., *Journal of Pharmaceutical Sciences*, vol. 60(11), p. 1760 (1971).
Newcome et al., *J. Org. Chem.* vol. 53, No. 23, pp. 5552–5554, (1988).
Krasnovskii et al., *Chem. Abstracts* 104:171364s (1986).
Index Chemicus, 17, 50586 (1965).
Heathcock et al., "A Stereoselective Total Synthesis of the Guaiazulenic Sesquiterpenoids α-Bulnesene and Bulnesol," Apr. 7, 1971, *J. Chem Soc.*
Ono et al, "DenitroHydrogenation of Aliphatic Nitro Compounds and New Use of Aliphatic Nitro Compounds as Radical Precursors," 1985, *Tetrahedron*, vol. 41, No. 19, pp. 4013–4023.
Brown et al., "Reaction of Diborane in Tetrahydrofuran Unit Selected Organic Compounds Containing Representative Functional Groups," Mar. 25, 1970, *J. Chem. Soc.*

*Primary Examiner*—Glennon H. Hollrah
*Assistant Examiner*—Scott C. Rand
*Attorney, Agent, or Firm*—Reising, Ethington, Barnard, Perry & Milton

[57] ABSTRACT

The bis-homotris compounds 4-amino-4-[1-(3-hydroxypropyl)]-1,7-heptanediol and 4-[1-(3-aminopropyl)]-4-[1-(3-hydroxypropyl)]-1, 7-heptanediol, and organic synthetic methods for their preparation are described. Unique multifunctional aminotriols, as well as their percursors, quaternary nitroalkanes are disclosed as building blocks for unimolecular micelles, as well as new series of cascade polymers. The quaternary nitro compounds which are disclosed allow the synthesis of a new aminotriol containing a quaternary carbon.

4 Claims, No Drawings

5,136,096

MULTIFUNCTIONAL SYNTHONS AS USED IN THE PREPARATION OF CASCADE POLYMERS OR UNIMOLECULAR MICELLES

This application is a continuation of application Ser. No. 401,323, filed Aug. 31, 1989, now abandoned.

TECHNICAL FIELD

This invention relates to the chemical field of aminoalkyltriols in general and to the chemical field of bis-homotris compounds in particular. It also relates to the synthons used in the preparation of a novel class of micelles or cascade polymers. It further concerns the preparation and usefulness of a group of chemicals which permit the creation of multifunctional, multi-tiered cascade polymers.

BACKGROUND ART

Micelles, which have many biotechnological uses, may be constructed as unimolecular structures with cascade methodology utilizing a series of chemical reactions in which building block molecules of the effective structure

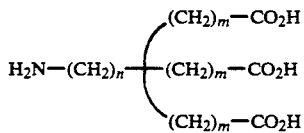

are reacted to form inter amide bonds between amino and carboxyl groups of different molecules. Initial cascade polymers have been shown to form aqueous [Newkome et al., J. Chem. Soc., Chem. Commun., 1986, 752] and non-aqueous [Baker, G.R., Dissertation, L.S.U., 1989] gels which possess properties suitable to a diverse range of applications which include, but are not limited to, bacteriological, growth, microscopy media, cosmetics and toiletries, drilling muds for oil production, textile printing (such as dye paste), foods, glazes, inks, lattices, lubricants, paints, pharmaceuticals, and agricultural [Molynenx, P., Chemistry and Technology of Water-Soluable Polymers; Plenum: New York, 1983, 113-114].

The literature indicates a number multi-armed and/or polybranched compounds, which include polypods, [Fornasier et al., Tet. Lett., 1976, 1381 and Vögtle et al., Chem. Ber., 1979, 112, 899]; hydrophillic lipids [Heiman and Vögtle, Annalen, 1980, 858]; octapus and hexapus molecules [Murakami et al., J. Chem. Soc., Perkin 1, 1981, 2800]; tentacle molecules [Suckling, C. J., J. Chem. Soc., Chem. Commun., 1982, 661] hexahost [MacNicol et al., J. Chem. Soc., Chem. Commun., 1976, 494]; branched polyamines [Geue et al., Aust. J. Chem., 1983 36, 927]; many-armed acyclic polyethers [Vögtle et al., Angew. Chem., Int. Eng. Ed., 1974, 13, 814]; starburst-dentritic macromolecules [Tomalia et al., Polym. J., 1985, 17, 117]; starburst polyether dendrimers [Hall, Tomalia et al., J. Org. Chem., 1987, 52, 5305]; noncyclic polyaza compounds [Vögtle et al., Synth., 1978, 155], and U.S. Pat. No. 4,507,466, issued Mar. 26, 1985. However, such compounds are: 1) difficult to prepare as evidenced by the required harsh conditions, 2) insufficiently soluble in aqueous solutions for some applications, 3) irregular in their molecular construction, and 4) susceptible to decomposition under mild conditions (in some instances yield, or include, toxic by-products).

Due to their unique construction, the new monomeric compounds of the present invention circumvents these problems by allowing mild functional group interconversion and alkylation, with even sterically demanding nucleophiles, of the building block termini. Specifically, the three carbon distance, which each terminus is displaced from the quaternary carbon center of branching, makes this possible. The literature indicates a lesser distance of separation to be unacceptable for nucleophilic substitution at multiple reaction sites equidistant from a center of branching [Rice et al., J. Pharm. Sci., 1971, 60, 1760].

The juxtaposition of reactive site termini relative to branching points in the invention allows the preparation of new cascade polymers based on a multiplicative and repetitive methodology which incorporates amidation, functional group interconversion, and alkylation (nucleophilic substitution) [Newkome et al., J. Am. Chem. Soc., 1986, 108, 849 and Newkome et al., J. Org. Chem., 1985, 50, 2003].

DISCLOSURE OF INVENTION

Therefore, an object of this invention is to provide novel compositions of matter which are useful as synthons or "building blocks" for cascade polymers.

Another object of this invention is the usefulness of new aminotriols as pH buffers in aqueous solution. This is due to the functional equivalency of the aminotriols to tris(hydroxymethyl) aminomethane which is employed extensively as a pH buffer.

This invention is comprised of the new compositions of matter and methods for the preparation of compounds of the structures

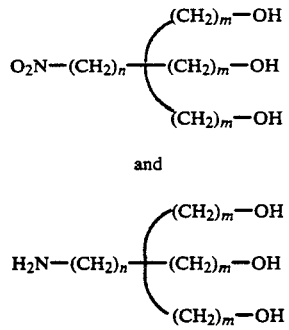

and

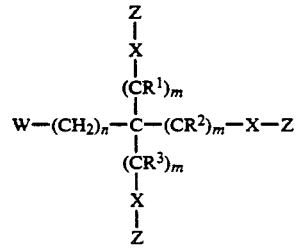

These compounds are important intermediates for the synthesis of the desired cascade building blocks (Newkome, Moorefield, and Theriot, J. Org. Chem., 1988, 53, 5552).

More broadly, however, this invention claims novel compounds of the formula $$\begin{array}{c} Z \\ | \\ X \\ | \\ (CR^1)_m \\ | \\ W-(CH_2)_n-C-(CR^2)_m-X-Z \\ | \\ (CR^3)_m \\ | \\ X \\ | \\ Z \end{array}$$

wherein
W is
NO$_2$, NH$_2$;
R$^1$ is
H$_2$,
lower alkyl,
aryl,
aralkyl,
halogen, or
cyano;
R$^2$ and R$^3$ may be the same or different;
R$^1$ and R$^2$ may not both be aryl;
X is
O,
NH, or
S; and,
Z is
H,
lower alkyl,
aralkyl,
carboxyl, or,
carbamoyl.
and of the formula

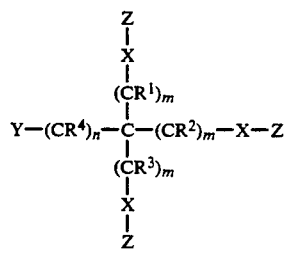

cyano;
R$^2$ and R$^3$ may be the same or different;
R$^1$ and R$^2$ may not both be aryl;
R$^4$ may be R$^1$, R$^2$ or R$^3$;
X is
O,
NH, or
S;
Z is
H,
lower alkyl,
aralkyl,
carboxyl, or
carbamoyl; and,
Y is
cyano,
formyl,
alkoxyformyl,
aralkoxyformyl,
nitro,
sulfoxo,
sulfonyl,
aminoformyl,
alkylaminoformyl,
arylaminoformyl,
aralkylaminoformyl,
alkyformyl,
arylformyl,
aralkylformyl,
aminomethyl,
hydroxymethyl, or
thiomethyl.

The present invention as to its novel compounds and novel methods of preparation are shown in the accompanying schematic diagram.

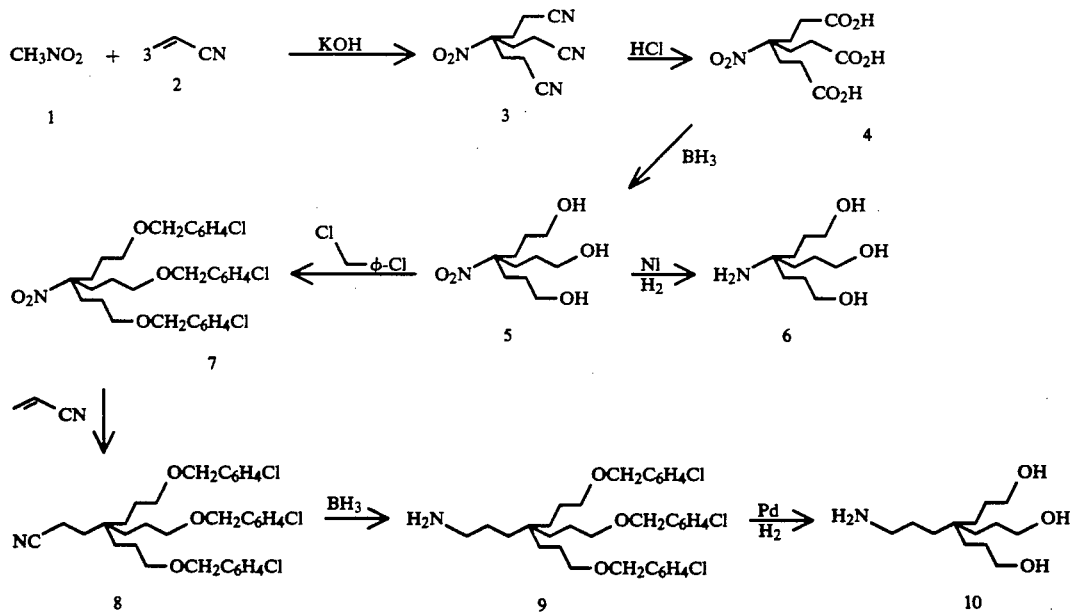

wherein
R$^1$ is
H,
lower alkyl,
aryl,
aralkyl,
halogen, or

Nitromethane (1) and three equivalents of acrylonitrile (2) are reacted under basic conditions to give the nitroalkylnitrile (3). The quaternary carbon of nitrile (3) and subsequent compounds is shown in an unrealistic conformation for clarity. The nitrile (3) is oxidized under acidic conditions to the tricarboxylic acid (4). The tricarboxylic acid (4) is reduced with boron trihydride to the nitroalkyltriol (5). The nitro group of triol (5) is reduced with hydrogen and nickel to give the aminoalkyltriol "bis-homotris" (6). Alternately, the nitroalkyltriol (5) is reacted with 4-chlorobenzyl chloride to "protect" the hydroxyl groups by conversion of the triol to the triether (7). The triether (7) is then reacted with acrylonitrile to give the corresponding β-cyanoethyl triether (8). The cyano triether (8) is reduced with boron trihydride to give the amino triether (9). Finally, the amino triether (9) is reduced with hydrogen and palladium to give the aminoalkyltriol "extended bis-homotris" (10).

BEST MODES FOR CARRYING OUT THE INVENTION

This invention incorporates the unique units, A and B, which are composed of a centrally located carbon attached preferably to three or four n-propyl alkyl chains. The separation of the

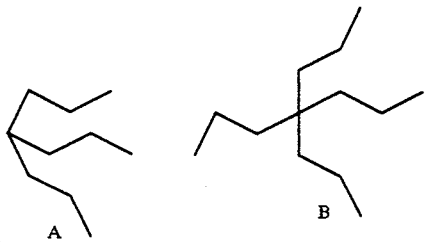

termini, or reaction centers, affords these units the novel characteristics desirable for synthesizing high molecular weight, cascade polymers comprised of repeating moieties of definite size and shape, which ultimately impose a definite size, and shape to the object of the syntheses, specifically, the cascade molecules.

The difficulty of ready translation to structural formulas of the complicated systematic names of the compounds dictates the use of a less cumbersome method. Structural formulas will be identified by unique numbers and specific molecular entities will be related to their structures via these numbers.

Melting point data were obtained from samples in capillary tubes with a Gallenkamp melting point apparatus (MFR-595) and are uncorrected. $^1H$ and $^{13}C$ NMR data were recorded on an IBM NR-80 spectrophotometer and were obtained in $Me_2$ $\delta SO$-$d_6$ solutions with $Me_4Si$, as the internal standard, unless otherwise indicated. Mass spectral (MS) data were obtained at 70 eV on a Finnigan 4510 GC-mass spectrophotometer (assignment, relative intensity). IR data were obtained on an IBM IR30 spectrophotometer.

Preparation of Tris (β-cyanoethyl) nitromethane (3)

This compound was prepared by the procedure of Bruson and Riener (1943) except that a solution of KOH (4.5 g) in $H_2O$ (10 mL) was added, in one portion, to a stirred solution of 20 g of nitromethane (1), 100 mL of dioxane, 100mL of acrylonitrile (2), tetrabutylammonium hydrogen sulfate (12 g), and $H_2O$ (10–20 mL). Caution: This reaction is very exothermic and should only be performed in a well ventilated hood. Application of the ice-water bath should commence at or near 50°–60° C.: mp 116.0°–118.0° C. ($CH_3CN/CHCl_3$) (lit. mp 114° C.); 84%; $^1H$ NMR δ 2.30 (m, $CH^3C$ N, 6 H), 2.60 (m, $CH_2CH_2C$ N,6 H; IR 2249,1607, 1487 cm$^{-1}$; $^{13}C$ NMR δ 119.3 (C N), 91.0 ($CNO_2$), 2.93 ($CH_2CH_2C$ N), 11.5 ($CH_2C$ N); MS, m/e 174 (M+ −$NO_2$, 94).

Preparation of 4-[1-(2-Carboxyethyl)]-4-nitroheptanedioic Acid (4)

A mixture of nitrile 3 (15.0 g) and concentrated HCl (65 mL) was refluxed 45 min and then cooled to 5° C. The white solid was filtered, and washed with (4×150 mL) cold $H_2O$ and dried in vacuo for 18–24 h to give (94%) the pure acid: 17.7 g; mp 183.0–185.5° C. (lit. mp 186° C.); $^1H$ NMR δ 2.18 (s, $CH_2CH_2CO_2H$, 12 H), 11.58 (br s, $CO_2H$, 3H); IR (Nujol mull) 3450–2500, 1701, 1532, 1458, 947 cm$^{-1}$; $^{13}C$ NMR 173.7 (C O), 28.5 ($CH_2CO_2H$); MS, m/e 260 (M+ −OH, 1).

Preparation of 4-Nitro-4-[1-(3-hydroxypropyl)]-1,7-heptanediol (5)

A stirred tetrahydrofuran (50 mL, dried over Na; 24 h) solution of triacid 4 (1.0 g, 3.6 mmol ) was cooled to 0° C. with an ice-salt bath, and a $BH_3$-THF solution (1.0 M; 11.9 mL, 11.9 mmol ) was added dropwise. After formation of a white precipitate, the temperature was allowed to rise to 25° C. Stirring was continued another 30 min at which time $H_2O$ was slowly added until the solid had disappeared. Saturated $NaHCO_3$ (25 ml) was then added, and the solvent was removed in vacuo. The viscous slurry was dried in vacuo; the resultant solid was triturated with hot absolute ethanol (3×60 mL) and filtered. The combined organic extract was concentrated to give (95%) of the pure nitro triol: 80 mg; bp 150° C. (0.3 mm) dec; $^1H$ NMR 1.30 (m, $CHCH_2OH$), 6H), 1.92 (m, $CH_2CH_2CH_2OH$ 6H), 3.39 (t, $CH_2OH$, J=6.0 Hz, 6H), 4.12 (br s, OH, 3H); IR (neat) 3600–3050, 1533, 1454, 1061 cm$^{-1}$; $^{13}C$ NMR δ 94.7 ($CNO_2$), 60.6 ($CH_2OH$), 31.2 ($CH_2CH_2CH_2OH$), 26.8 ($CH_2CH_2OH$); MS, m/e 189 (M+ −$NO_2$, 6). Anal. Calcd for $C_{10}H_2NO_5$: 51.06; H, 8.94; N, 5.96. Found: C, 50.89; H, 8.85; N, 5.99.

Preparation of Bis-homotris: 4-Amino-4[1-(3-hydroxypropyl)]-1, 7-heptanediol (6)

A solution of nitro triol 5 (4.7 g, 20 mmol), absolute EtOH (150mL) and T-1 Raney $Ni^{23}$ (2–3 g) was reduced under a $H_2$ atmosphere in a Parr hydrogenator at 3 atm for 72 h at 25° C. or until hydrogen uptake subsided. The catalyst was cautiously filtered through a Celite pad (pyrophonic when dry). The solvent was removed in vacuo, and the resultant viscous liquid was dried in vacuo to yield (98%) of the crude amino triol (4.1 g) which was distilled (Kugelrohr) to afford (82%) of bis-homotris, a colorless solid: 3.4 g; bp 220°–235° C. (0.5 mm); mp 108.5°–109.8° C.; $^1H$ NMR (D20, dioxane; 3.70) 1.37 (s, $CH_2CH_2CH_2OH$, 12H), 3.54 (t, $CH_2OH$, J=5.4 Hz, 6H); IR (Nujol mull) 3500–2900, 3330, 3287, 1620, 1224, 1064 cm$^{-1}$; $^{13}C$ NMR 61.7 ($CH_2OH$), 52.4 ($CNH_2$), 36.3 ($CH_2CH_2CH_2OH$), 26.8 ($CH_2CH_2OH$); MS m/e 206 (M+ +H, 1). Anal. Calcd for $C_{10}H_{23}NO_3$; C, 58.54; H, 11.22; N, 6.83. Found: C, 58.48; H, 11.12; N, 6.70.

Preparation of 4-Nitro-4[1-(3-(4-chlorobenzyloxy)) propyl]bis-1,7,-(4-chlorobenzyloxy)heptane(7)

Protection of the nitrotriol was accomplished via the general procedure of Heathcock and Ratcliffe (1971). To a stirred solution of nitro triol 5 (8.1 g, 35 mmol) and dimethyl sulfoxide (250 mL) was added NaH (2.8 g, 115 mmol). After stirring 30 min at 25° C., 4-chlorobenzyl chloride (18.6 g, 115 mmol) was added in a 50% solution in dimethyl sulfoxide over a period of ½ h. The resulting mixture was stirred and benzene (250mL) was added which was washed with $H_2O$ (2×150 mL) and saturated brine (2×150 mL). Drying with $MgSO_4$, and removal of the solvent gave (17.6 g, 83%) the crude product. Purification via silica gel afforded (58%) the nitro triether 7 as a colorless oil: 12.3 g; $^1H$ NMR ($CDCl_3$) 1.20–2.25 (m, $CH_2CH_2CH_2O$, 12H), 3.44 (t, $CH_2CH_2CH_2O$, J=5.6 Hz, 6H), 4.46 (s, $OCH_2C_6H_4Cl$, 6H), 7.30 (s, $C_6H_4Cl$, 12H); $^{13}C$ NMR ($CDCl_3$) 136.9, 133.4, 128.9, 128.5 ), 94.1 ($O_2NC$), 72.0 ($CH_2C_6H_4Cl$), 69.6 ($CH_2CH_2CH_2O$), 32.2 ($CH_2CH_2CH_2O$), 23.9 ($CH_2CH_2CH_2O$); IR (neat) 30.53, 2940, 2862, 1599, 1579, 1089, 1016, 808 cm$^{-1}$; MS, m/e 295 ($M^+ - C_{14}H_{12}Cl_2NO_3$, 5). Anal. Calcd. for $C_{31}H_{36}Cl_3NO_5$: C, 61.14; H, 5.95; N, 2.30. Found: C, 61.03; H, 5.79; N, 2.27.

Preparation of 4-[1-(2-Cyanoethyl)]-4-[1-3(4-chlorobenzyloxy)) propyl]-bis-1,7-(4-chlorobenzyloxy) heptane (8)

Nitrile 8 was prepared via the procedure of Ono, Miyake, Kamimura, Hamamoto, Tamura, and Kaji (1985). A solution of nitro triether 7 (2.4 g, 4 mmol), tri-n-butyltin hydride (3.5 g, 12 mmol), acrylonitrile (2.3 g, 44 mmol) 2,2'-azobis(2-methylproprionitrile), (0.66 g, 4 mmol), and toluene (10 mL) was heated at 100° C. for 30 min. Upon cooling to 25° C., ethyl acetate was added (100 mL) and the solid was removed via vacuum filtration. Removal of the solvent and subjection to silica gel chromatography gave (52%) of the pure nitrile 8: 1.3 g; $^1H$ NMR δ 0.70–1.70 (m, $NCCH_2CH_2CCH_2CH_2CH_2ONCCCH_2$, 14H), 2.40–2.10 (m, NCCH, 2H), 3.40 (t, $CH_2CH_2CH_2O$, J=5.6 Hz, 6H), 4.42 (s, $CH_2C_6H_4Cl$, 6H), 7.25 (s, $C_6H_4Cl$, 12H); $^{13}C$ NMR δ 137.0, 133.2, 128.8, 128.4 ($C_6H_4Cl$), 120.1 (CN), 72.0 ($CH_2C_6H_4Cl$), 70.5 ($CH_2CH_2CH_2O$), 36.5 ($CCH_2CH_2CH_2$), 31.8 ($CH_2CH_2CH_2O$), 31.6 ($NCCH_2CH_2$), 23.1 ($CH_2CH_2CH_2$), 11.2 ($CH_2CN$); IR (neat) 3053, 2943, 2860, 2247, 1599, 1491, 1089, 1016, 808 cm$^{-1}$; MS, m/e 491 ($M^+ - CH_2C_6H_4Cl$, 2). Anal. Calcd. for $C_{34}H_{40}Cl_3NO_3$: C, 66.18; H, 6.53; N, 2.27. Found: C, 65.96; H, 6.63; N, 2.46.

Preparation of 4-1-(3-Aminopropyl)]-4-[1-(3-(4-chlorobenzyloxy)) propyl]-bis-1,7(4-chlorobenzyloxy))heptane (9)

Amine 9 was prepared by the procedure of Brown, Heim, and Yoon (1970). To a solution of nitrile 8 (0.3 g, 0.59 mmol) in THF (15 mL) at 0° C. under a nitrogen atmosphere was added $BH_3$-THF via syringe (1.0M; 1.9 mmol, 1.9 mL). After refluxing 12 h, the solution was cooled to 0° C. and quenched by the slow addition of $H_2O$ (1.0 mL). Upon the addition of 10% HCl, the solution was stirred for 1 h and subsequently made basic with $Na_2CO_3$. Evaporation to dryness and trituration with hot $CH_2Cl_2$, followed by filtration through Celite and removal of the solvent yielded (89%) the pure amine 9; 0.30 g; $^1H$ NMR ($CDCl_3$) δ 0.70–1.80 (m. $CCH_2CH_2CH_2$, 16 H), 2.73 (br s, $H_2NCH_2$, 2H), 3.38 (br s, $CH_2CH_2CH_2O$, 6H), 4.40 (s, $CH_2C_6H_4Cl$, 6H), 7.25 (s, $C_6H_4Cl$, 12H); $^{13}C$ NMR ($CDCl_3$) δ 137.2 133.2, 128.8, 128.5, ($C_6H_4Cl$), 72.0 ($CH_2C_6H_4Cl$), 71.2 ($CH_2CH_2CH_2O$), 42.8 ($H_2NCH_2$), 36.3 ($CCH_2CH_2CH_2$), 33.4 ($H_2NCH_2CH_2CH_2$), 32.5 ($CH_2CH_2CH_2O$), 27.1 ($H_2NCH_2CH_2CH_2$), 23.4 ($CH_2CH_2CH_2O$); IR (neat) 3368, 3308, 3047, 2941, 2860, 1599, 1491, 1089, 1016, 808 cm$^{-1}$; MS, m/e 125.5 ($M^+ - C_{32}H_{38}Cl_2NO_3$, 100). Anal. Calcd. for $C_{34}H_{44}Cl_3NO_3$: C, 65.75; H, 7.14; N, 2.25. Found: C, 65.82; H, 6.56; N, 2.56.

Preparation of Extended Bis-homotris: 4-[1-(3-Aminopropyl)]-4-[1-(3-hydroxypropyl)]-1,7-heptanediol (10)

Deprotection of the alcohols was accomplished by a known general procedure (Heathcock and Ratcliffe, 1971). To a glass bomb was added the amino triether 9 (0.20 g, 0.32 mmol), absolute EtOH (100 mL), and a catalytic amount of 20% Palladium on carbon ( 100 mg). The vessel was placed on a Parr hydrogenator, charged to 20 psi with $H_2$, for 5 h. The solvent was then removed, after filtration through Celite, to give (91%) the amino triol 10: 0.071 g; $^1H$ NMR ($D_2O$) δ 1.41 (br s, $CCH_2CH_2$, 16H), 3.00 (br s, $H_2NCH_2$), 3.64 (br s, $CH_2OH$, 6H); $^{13}C$ NMR ($D_2O$) δ 63.4 ($CH_2OH$), 41.3 ($CH_2NH_2$), 37.1 ($CCH_2CH_2CH_2$), 33.8 ($H_2NCH_2CH_2CH_2$), 33.1 ($CH_2CH_2CH_2OH$), 26.9 ($CH_2CH_2OH$), 22.1 ($H_2NCH_2CH_2$); IR (neat) 3650–2854, 2941, 2870, 1635, 1466, 1055 cm$^{-1}$; MS, m/e 248 ($M^+ +1$, 7). Anal. Calcd. for $C_{13}H_{29}NO_3$: C, 63.12; H, 11.82; N, 5.66. Found: C, 63.67; H, 12.01; N, 5.82.

Utilizing the methods of preparation of this invention, other novel compositions having beneficial properties should result. In its broadest concept, novel compositions comprise formulas bis-homotris as described wherein $R^1$ can be $H_2$; lower alkyl, preferably methyl or ethyl; aryl of 6 to 12 atoms, preferably phenyl; aralkyl of 7 to 20 carbon atoms, preferably benzyl; halogen such as fluoro, chloro, bromo, or iodo; or cyano; wherein $R^2$ and $R^3$ may be the same as $R^1$ or different, but $R^1$ and $R^2$ may not both be aryl; wherein X is O, NH, or S; and, wherein Z is hydrogen, alkyl of 1–8 carbon atoms, preferably methyl, ethyl, methoxymethyl or methoxyethoxymethyl; aralkyl preferably benzyl, p-chlorobenzyl, or p-methoxybenzyl; carboxyl preferably acetyl, benzoyl, or benzyloyl; or carbamoyl, preferably methyl or ethyl carbamoyl or benzyl carbamoyl. Preferably, n is 0 or 2, and m is 3.

In its broadest concept, novel compositions comprise formulas for extended bis-homotris as described wherein $R^1$ is hydrogen; lower alkyl of 1–8 carbon atoms, preferably methyl or ethyl; aryl of 6 to 12 carbon atoms, preferably phenyl; aralkyl of 7 to 20 carbon atoms, preferably benzyl; halogen such as fluoro, chloro, bromo, or iodo; or cyano; wherein $R^2$ and $R^3$ may be the same as $R^1$ or different, but $R^1$ and $R^2$ may not both be aryl; wherein $R^4$ may be $R^1$, $R^2$, or $R^3$; wherein X is O, NH or S; wherein Z is hydrogen; lower alkyl of 1–8 carbon atoms, preferably methyl, ethyl, methoxymethyl or methoxyethoxymethyl; aralkyl, preferably benzyl, p-chlorobenzyl, or p-methoxybenzyl; carboxyl, preferably acetyl, benzoyl, or benzyloyl; or carbamoyl, preferably methyl or ethyl carbamoyl or benzyl carbamoyl; wherein Y is cyano; formyl; alkoxyformyl, preferably methoxyformyl or ethoxyformyl; aralkoxyformyl, preferably benzyloxyformyl; nitro; sulfoxo; sulfonyl; animoformyl; alkylaminoformyl; arylaminoformyl; aralkylaminoformyl; alkylformyl; arylformyl; aralkylformyl; aminomethyl; hydroxymethyl; or thiomethyl. Preferably n is 0 or 2 or 3 and m is 3.

One particularly advantageous method of the present invention comprises the production of novel compound 4-[1-(3-aminopropyl)]-4-[1-(3-hydroxypropyl)]-1,7-heptanediol from intermediate starting material 4-nitro-4-[1-(3-hydroxylpropyl)]-1,7-heptanediol, described above. Utilizing the method of the present invention, similar results should be obtained to prepare a compound of the formula

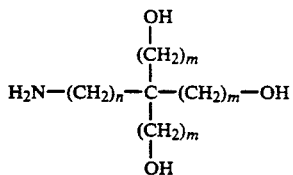

from a compound of the formula

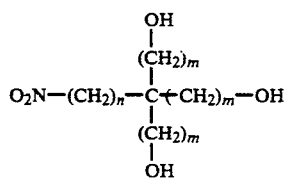

In one embodiment, n=0 and m=3, and 4-chlorobenzyl chloride is used to protect the hydroxyl groups. Preferably, n=2, m=3 and 4-chlorobenzyl chloride is used to protect the hydroxyl groups. The basic methodology countemplates starting materials as nitromethane and acrylonitrile to prepare the intermediate nitro triol.

What is claimed is:

1. A compound of the formula

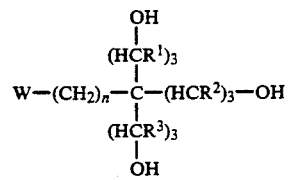

wherein W is NO$_2$, NH$_2$; R$^1$, R$_2$ and R$_3$ can be independently selected from the group consisting of H, lower alkyl, aryl, aralkyl, halogen, or cyano; R$^1$ and R$^2$ may not both be aryl; and n is 0, 2 or 3.

2. A compound as described in claim 1 wherein n is 1.
3. 4-[1-(3aminopropyl)]-4-[1-(3-hydroxypropyl)]-1,7-heptanediol.
4. 4-amino-4-[1-(3-hydroxypropyl)]-1,7-heptanediol.

* * * * *